(12) United States Patent
Brotman

(10) Patent No.: US 11,723,675 B2
(45) Date of Patent: *Aug. 15, 2023

(54) ADJUSTABLE DEPTH DRILL GUIDE

(71) Applicant: NuVasive, Inc., San Diego, CA (US)

(72) Inventor: Michael Brotman, San Diego, CA (US)

(73) Assignee: NuVasive, Inc., San Diego, CA (US)

(*) Notice: Subject to any disclaimer, the term of this patent is extended or adjusted under 35 U.S.C. 154(b) by 236 days.

This patent is subject to a terminal disclaimer.

(21) Appl. No.: 17/123,806

(22) Filed: Dec. 16, 2020

(65) Prior Publication Data

US 2021/0100566 A1 Apr. 8, 2021

Related U.S. Application Data

(63) Continuation of application No. 16/405,796, filed on May 7, 2019, now Pat. No. 10,898,207, which is a continuation of application No. 15/392,896, filed on Dec. 28, 2016, now Pat. No. 10,327,787.

(60) Provisional application No. 62/271,719, filed on Dec. 28, 2015.

(51) Int. Cl.
| | | |
|---|---|---|
| A61B 17/17 | (2006.01) | |
| A61B 17/70 | (2006.01) | |
| A61B 17/00 | (2006.01) | |
| A61B 90/00 | (2016.01) | |

(52) U.S. Cl.
CPC .......... *A61B 17/17* (2013.01); *A61B 17/7092* (2013.01); *A61B 2017/00991* (2013.01); *A61B 2090/034* (2016.02); *A61B 2090/036* (2016.02)

(58) Field of Classification Search
CPC ...... A61B 2017/00991; A61B 17/7092; A61B 17/17
See application file for complete search history.

(56) References Cited

U.S. PATENT DOCUMENTS

| | | | |
|---|---|---|---|
| 4,586,497 A | 5/1986 | Dapra et al. | |
| 5,409,493 A * | 4/1995 | Greenberg | ............ A61C 1/084 |
| | | | 606/86 R |
| 5,458,602 A | 10/1995 | Goble et al. | |
| 5,507,801 A | 4/1996 | Gisin et al. | |
| 5,613,971 A | 3/1997 | Lower et al. | |
| 5,851,207 A | 12/1998 | Cesarone | |
| 5,885,300 A | 3/1999 | Tokuhashi et al. | |
| 5,911,722 A | 6/1999 | Adler et al. | |
| 6,059,790 A | 5/2000 | Sand et al. | |
| 6,086,595 A | 7/2000 | Yonemura et al. | |
| 6,156,040 A | 12/2000 | Yonemura et al. | |

(Continued)

FOREIGN PATENT DOCUMENTS

| | | |
|---|---|---|
| AU | 2004281735 B2 | 5/2010 |
| CN | 202198637 U | 4/2012 |

(Continued)

*Primary Examiner* — Christian A Sevilla
(74) *Attorney, Agent, or Firm* — Hoffman Warnick LLC

(57) ABSTRACT

The present disclosure in one aspect provides an adjustable depth drill guide comprising a trigger assembly further comprising a trigger and a primary actuating element and a telescopic rotational assembly which abuts the primary actuating element and further comprises an intermediate actuating element. The drill guide described herein allows a surgeon to adjust the depth of the drill guide using only one hand while in-situ.

20 Claims, 22 Drawing Sheets

(56) References Cited

U.S. PATENT DOCUMENTS

| | | |
|---|---|---|
| 6,210,415 B1 | 4/2001 | Bester |
| 6,224,607 B1 | 5/2001 | Michelson |
| 6,238,400 B1 | 5/2001 | Bays |
| 6,287,313 B1 | 9/2001 | Sasso |
| 6,342,057 B1 | 1/2002 | Brace et al. |
| 6,379,364 B1 | 4/2002 | Brace et al. |
| 6,391,016 B2 | 5/2002 | Bays |
| 6,391,017 B2 | 5/2002 | Bays |
| 6,524,318 B1 | 2/2003 | Longhini et al. |
| 6,562,041 B1 | 5/2003 | Yonemura et al. |
| 6,562,046 B2 | 5/2003 | Sasso |
| 6,669,698 B1 | 12/2003 | Tromanhauser et al. |
| RE38,684 E | 1/2005 | Cesarone |
| 6,929,647 B2 | 8/2005 | Cohen |
| 6,960,216 B2 | 11/2005 | Kolb et al. |
| 7,060,068 B2 | 6/2006 | Tromanhauser et al. |
| 7,081,119 B2 | 7/2006 | Stihl |
| 7,131,974 B2 | 11/2006 | Keyer et al. |
| 7,210,881 B2 | 5/2007 | Greenberg |
| 7,226,452 B2 | 6/2007 | Zubok et al. |
| 7,278,997 B1 | 10/2007 | Mueller et al. |
| 7,326,200 B2 | 2/2008 | Trieu et al. |
| 7,357,804 B2 | 4/2008 | Binder, Jr. et al. |
| 7,442,197 B2 | 10/2008 | Abdelgany |
| 7,491,209 B2 | 2/2009 | Mueller et al. |
| 7,513,722 B2 | 4/2009 | Greenberg et al. |
| 7,618,439 B2 | 11/2009 | Zubok et al. |
| 7,637,911 B2 | 12/2009 | Zubok et al. |
| 7,641,654 B2 | 1/2010 | Zubok et al. |
| 7,641,665 B2 | 1/2010 | Zubok et al. |
| 7,648,511 B2 | 1/2010 | Zubok et al. |
| 7,674,292 B2 | 3/2010 | Zubok et al. |
| 7,708,780 B2 | 5/2010 | Zubok et al. |
| 7,731,721 B2 | 6/2010 | Rathbun et al. |
| 7,776,047 B2 | 8/2010 | Fanger et al. |
| 7,985,229 B2 | 7/2011 | Stihl |
| 8,172,854 B2 | 5/2012 | Blain et al. |
| 8,282,642 B2 | 10/2012 | McClintock et al. |
| 8,323,292 B2 | 12/2012 | Dudasik et al. |
| 8,353,938 B2 | 1/2013 | Trieu et al. |
| 8,465,491 B2 | 6/2013 | Yedlicka et al. |
| 8,480,673 B2 | 7/2013 | Yedlicka et al. |
| 10,898,207 B2 * | 1/2021 | Brotman ................ A61B 17/17 |
| 2003/0233098 A1 | 12/2003 | Markworth |
| 2007/0093848 A1 | 4/2007 | Harris et al. |
| 2007/0233150 A1 | 10/2007 | Blain et al. |
| 2009/0254094 A1 | 10/2009 | Knapp et al. |
| 2010/0145340 A1 | 6/2010 | Phan et al. |
| 2011/0138605 A1 | 6/2011 | Swift et al. |
| 2012/0046749 A1 | 2/2012 | Tatsumi |
| 2012/0123417 A1 | 5/2012 | Smith |
| 2012/0215232 A1 | 8/2012 | Olsen et al. |
| 2013/0012945 A1 | 1/2013 | Chreene et al. |

FOREIGN PATENT DOCUMENTS

| | | |
|---|---|---|
| KR | 20110138605 A | 12/2011 |
| KR | 101110107 B1 | 1/2012 |

\* cited by examiner

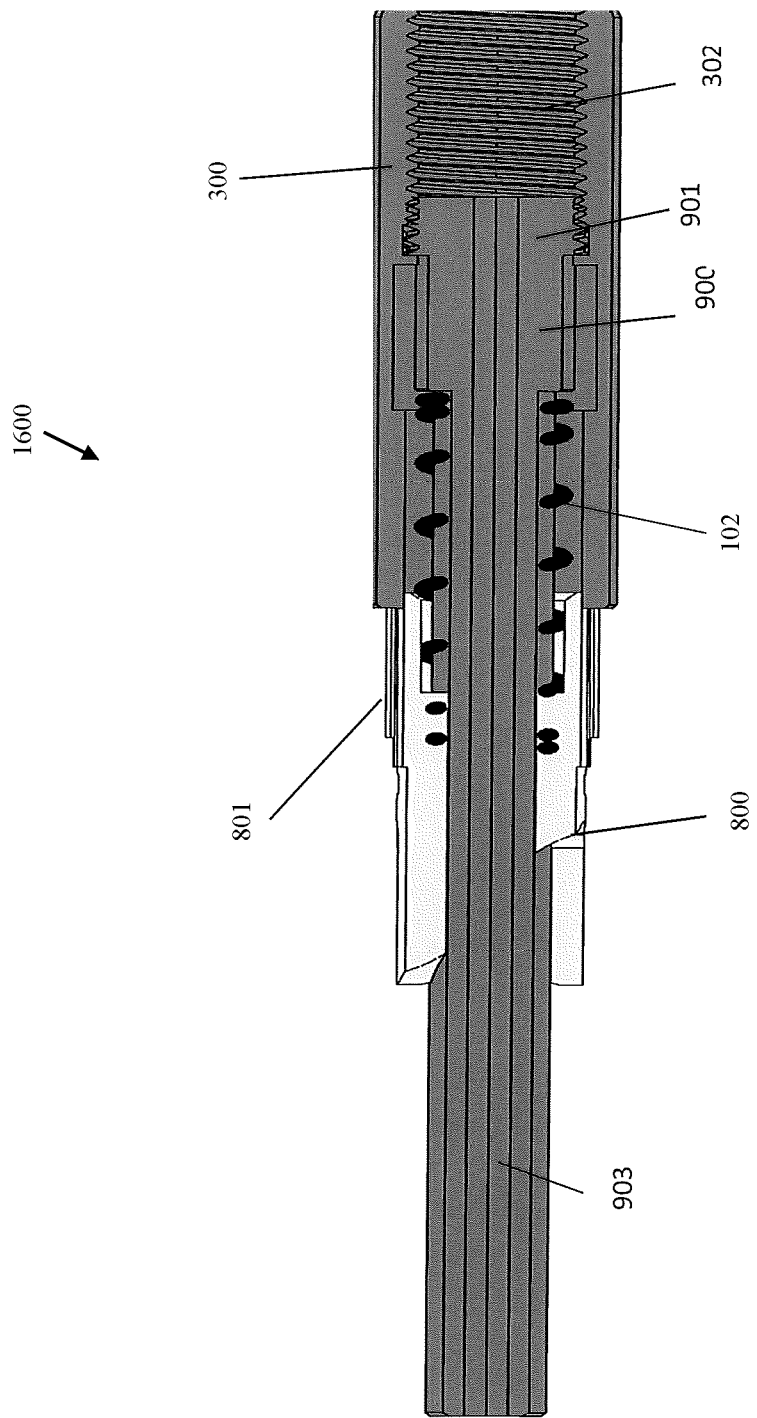

ADJUSTABLE DEPTH DRILL GUIDE

CROSS-REFERENCE TO RELATED APPLICATIONS

This application is a continuation of U.S. patent application Ser. No. 16/405,796 filed May 7, 2019, which is a continuation of U.S. patent application Ser. No. 15/392,896 filed Dec. 28, 2016, which claims priority to U.S. Provisional Patent Application No. 62/271,719 filed on Dec. 28, 2015, the entire contents of which are each hereby expressly incorporated by reference into this disclosure as if set forth in its entirety herein.

FIELD OF INVENTION

The field of the invention generally relates to adjustable depth drill guides for medical instruments for use in surgical applications requiring precision depth adjustment.

BACKGROUND

Drill guides are often used to assist surgeons in creating a pilot hole prior to screw insertion as the drill guides allow greater precision and control while create the pilot hole. During posterior cervical surgical procedures for example, drill guides are used to assist the surgeon setting the depth of the pilot hole, based on the length of the screw, to ensure the hole is drilled at the proper depth. Typically, this often requires that the surgeon estimate the appropriate length for the screw, preset the guide to the appropriate depth based on the bone screw size estimation, place the guide in the surgical opening, and finally drill the pilot hole. Subsequently, the surgeon may take a series of real-time X-rays to determine if the pilot hole depth is sufficient. If it is not, the surgeon must remove the drill guide, reset the drill guide to the appropriate length, and reintroduce the instrument to the surgical wound or opening. This can be time-consuming, creates numerous opportunities for error, and increases the risk of infection.

In order to make real-time adjustments without removing the drill guide from the surgical opening, surgeons must be afforded the luxury of using a drill guide that requires the use of only one hand to make any necessary incremental adjustments to increase hole depth. As the drill guide is operable by using only one hand, instead of two as described in prior art, the surgeon is able to adjust the depth of the drill guide with one hand while maintaining the drill in the other hand. This is important as it prevents the necessity of removing the drill guide from the surgical opening and the instrument can remain in-situ. The drill guide described herein, allows the surgeon to introduce the drill guide into the surgical area and adjust the depth as necessary with one squeeze of the trigger, thus, addressing the need to make real-time adjustments within the surgical area.

SUMMARY

Disclosed herein is a drill guide for use in surgery. In one embodiment, an adjustable depth drill guide is provided comprising a shell, a trigger assembly, and a telescopic rotational assembly. The shell of the drill guide is comprised of a handle, a frame, a drill stop, and a shaft. Enclosed in the shell of the drill guide is first, the trigger assembly, comprised of a primary actuating element, a trigger, and a distal spring. Finally, the drill guide includes a telescopic rotational assembly, comprised of an inner guide, a sheath, an intermediate actuating element, and a proximal spring.

The drill guide has a proximal and distal end. A frame is attached to the upper portion of the handle and extends horizontally along the length of the device, ultimately forming a vertical member with an opening. Additionally, the shaft and drill stop combine with the handle and frame to form the shell of the drill guide, enclosing the trigger assembly and telescopic rotational assembly.

Upon pulling the trigger, the primary actuating element begins to translate proximally toward the intermediate actuating element. The translation of the primary actuating element in turn, causes the intermediate actuating element to translate proximally toward the proximal end of the drill guide within the sheath. Once the intermediate actuating element reaches a certain point, the intermediate actuating element rotates 180 degrees. This rotation causes the sheath to rotate clockwise along the inner guide. The rotation of the sheath results in the sheath translating toward the distal portion of the drill guide an incremental distance and thus, the drill stop translates an identical distance. The surgeon may reverse this action by rotating the drill stop counter-clockwise. This counter-clockwise rotation reverses the rotation of the sheath and intermediate actuating element, reducing the depth of the drill guide an incremental distance. The surgeon can repeat either action within the bounds of the drill guide, with one hand, and without moving the drill guide from the surgical area.

According to another embodiment, an adjustable depth drill guide is described. The drill guide is also fitted with a modular sleeve that may be affixed to the vertical element of the frame.

BRIEF DESCRIPTION OF DRAWINGS

FIG. 8 illustrates a cross sectional view of the sheath, inner guide, proximal spring and intermediate actuating element as described in one embodiment of the drill guide of the present disclosure.

DETAILED DESCRIPTION

Figure 1:
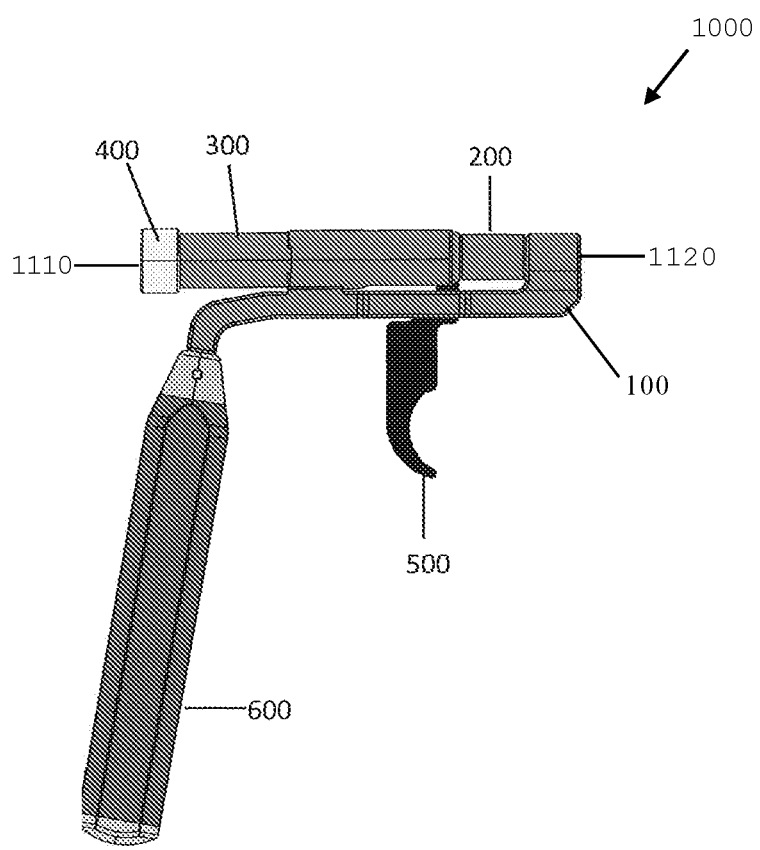
FIG. 1 illustrates a side view of one embodiment of the drill guide of the present disclosure.

Unless otherwise defined, all terms (including technical and scientific terms) used herein have the same meaning as commonly understood by one of ordinary skill in the art of this disclosure. It will be further understood that terms, such as those defined in commonly used dictionaries, should be interpreted as having a meaning that is consistent with their meaning in the context of the specification and should not be interpreted in an idealized or overly formal sense unless expressly so defined herein. Well known functions or constructions may not be described in detail for brevity or clarity.

The terminology used herein is for the purpose of describing particular embodiments only and is not intended to be limiting. As used herein, the singular forms "a", "an" and "the" are intended to include the plural forms as well, unless the context clearly indicates otherwise.

Spatially relative terms, such as "under", "below", "lower", "over", "upper" and the like, may be used herein for ease of description to describe one element or feature's relationship to another when the apparatus is right side up.

The terms "about" and "approximately" shall generally mean an acceptable degree of error or variation for the quantity measured given the nature or precision of the measurements. Typically, exemplary degrees of error or variation are within 20 percent (%), preferably within 10%, and more preferably within 5% of a given value or range of values. Numerical quantities given herein are approximate unless stated otherwise, meaning that the term "about" or "approximately" can be inferred when not expressly stated.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

While the subject matter is susceptible to various modifications and alternative forms, specific embodiments thereof have been shown by way of example in the drawings and are herein described in detail. It should be understood, however, that the description herein of specific embodiments is not intended to limit the subject matter to the particular forms disclosed, but on the contrary, the subject matter is to cover all modifications, equivalents, and alternatives falling within the spirit and scope of the subject matter as defined herein. For example, any of the features of a particular example described herein may be used with any other example described herein without departing from the scope of the present subject matter.

The present disclosure provides an adjustable depth drill guide 1000 that allows surgeons to make incremental depth adjustments in small increments when drilling pilot holes prior to bone screw placement. In the embodiment shown in FIGS. 1-3, 5, and 8 the adjustable depth drill guide 1000 comprises: a shell 1200, a trigger assembly 1500, and a telescopic rotational assembly 1600.

Figure 3:
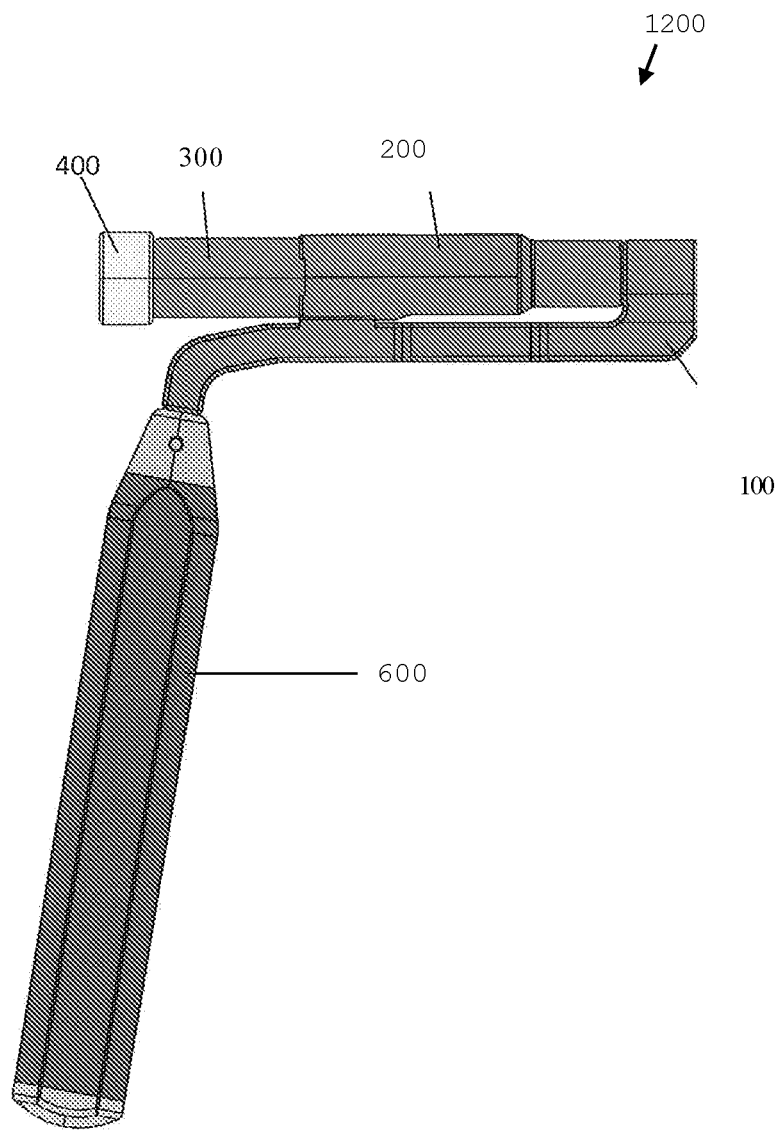
FIG. 3 illustrates a side view of the shell of one embodiment of the drill guide.

The shell 1200 of the drill guide 1000 is comprised of a handle 600, a frame 100, a drill stop 400, and a shaft 200. As shown in FIG. 3 the shell 1200 provides the outer shape of the drill guide 1000. The handle 600 provides a hand-hold for the surgeon and allows the surgeon to navigate the drill guide 1000 and guide it into the proper space. Immediately above and connected to the upper portion of the handle 600 is the frame 100.

The frame 100 is comprised of a generally horizontal portion 116 extending from the top portion of the handle 600 laterally toward the distal end 120 of the drill guide 1000. As illustrated in FIGS. 4A-D, the horizontal portion has a length 106, width 109, and height 112. The height 112 and length 106, are sized to accommodate the trigger 500. Likewise, the width 109 must also be a sufficient distance so as to accommodate the dimensions of the trigger 500.

Figure 4A:
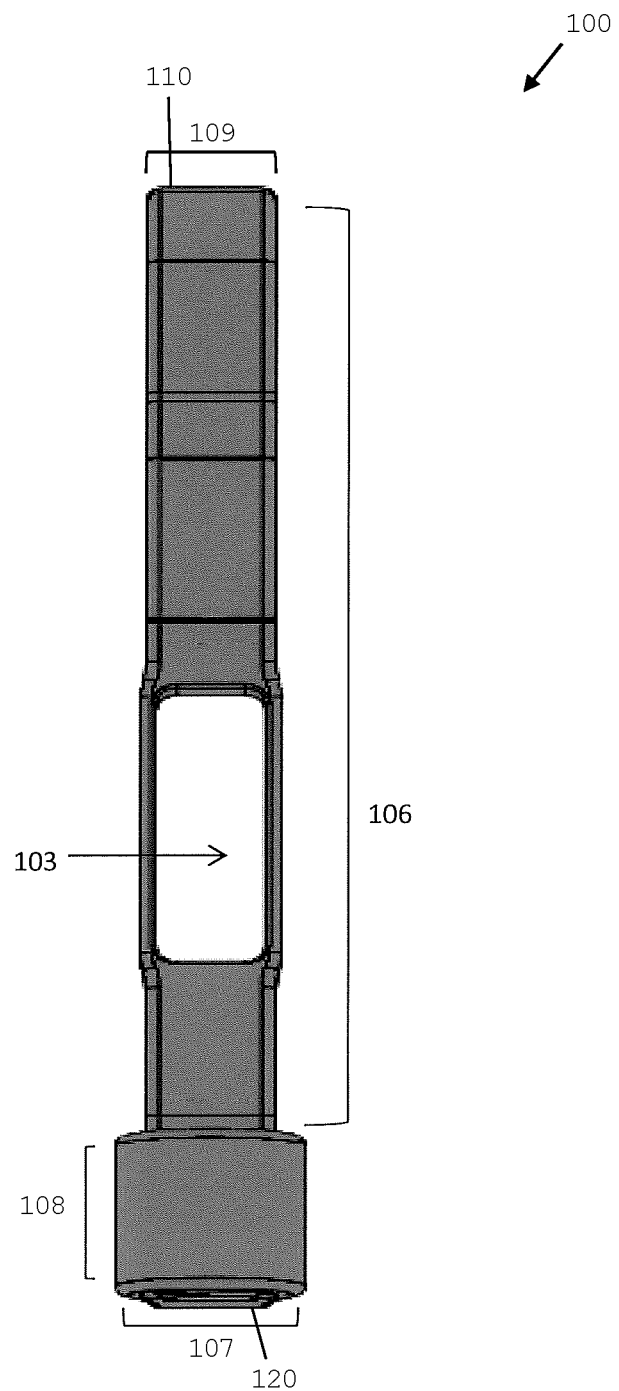
FIG. 4A illustrates a top view of the frame as described in one embodiment of the drill guide of the present disclosure.
Figure 4B:
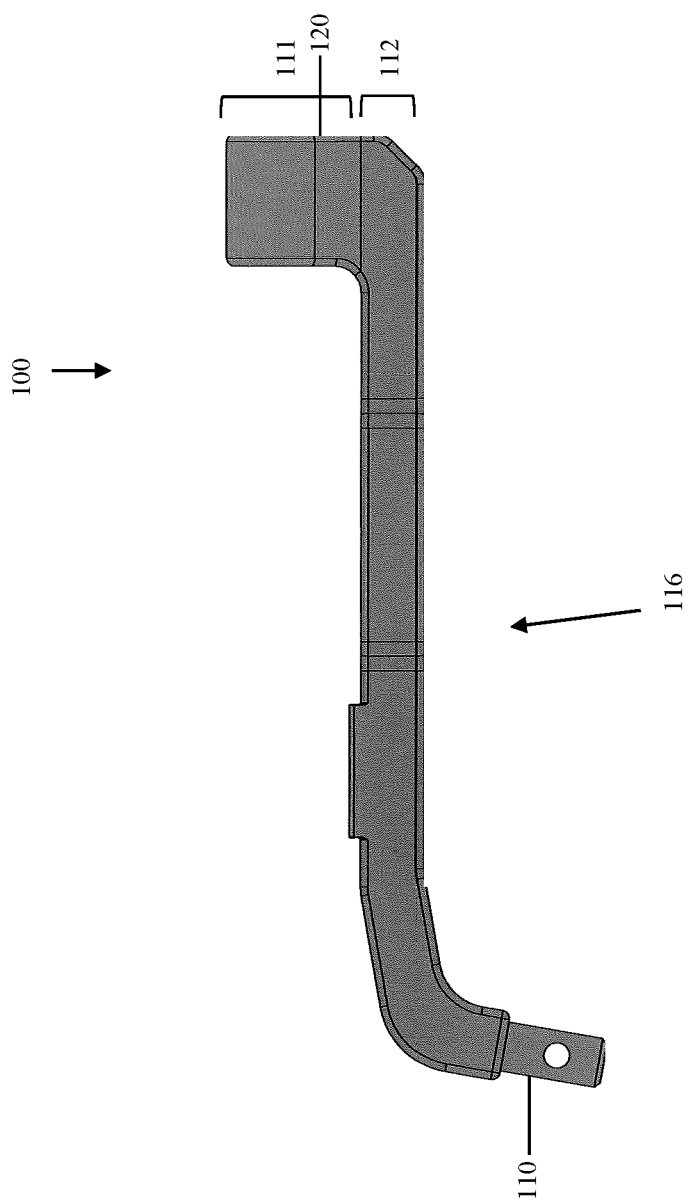
FIG. 4B illustrates a side view of the frame as described in one embodiment of the drill guide of the present disclosure.
Figure 4C:
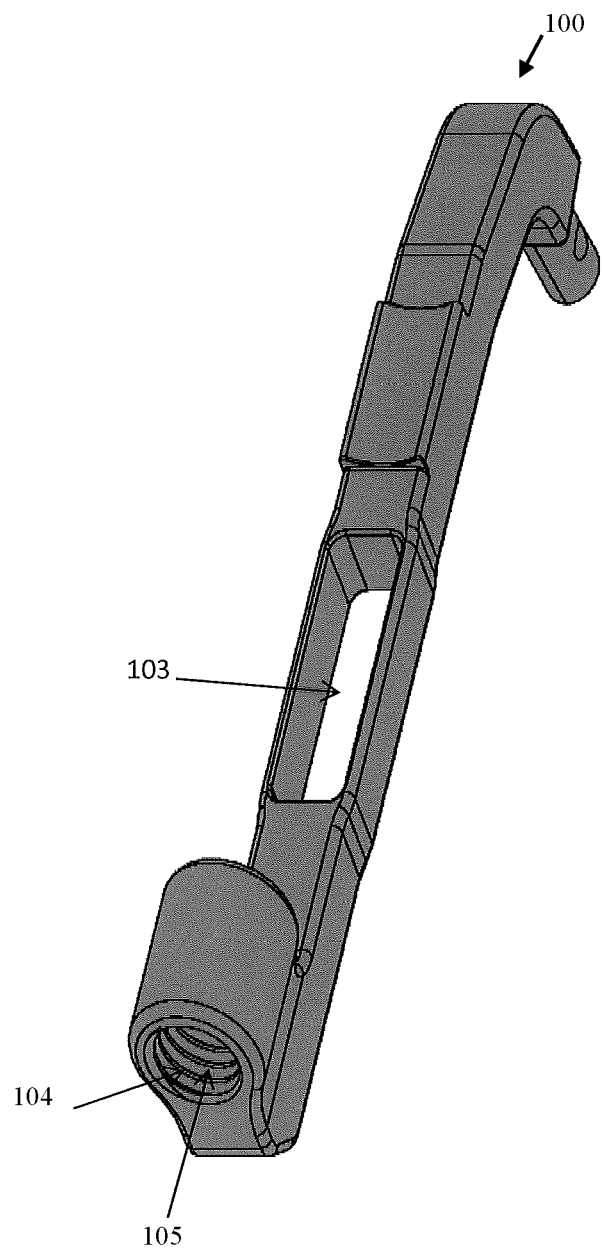
FIG. 4C illustrates an isometric view of the frame as described in one embodiment of the drill guide of the present disclosure.
Figure 4D:
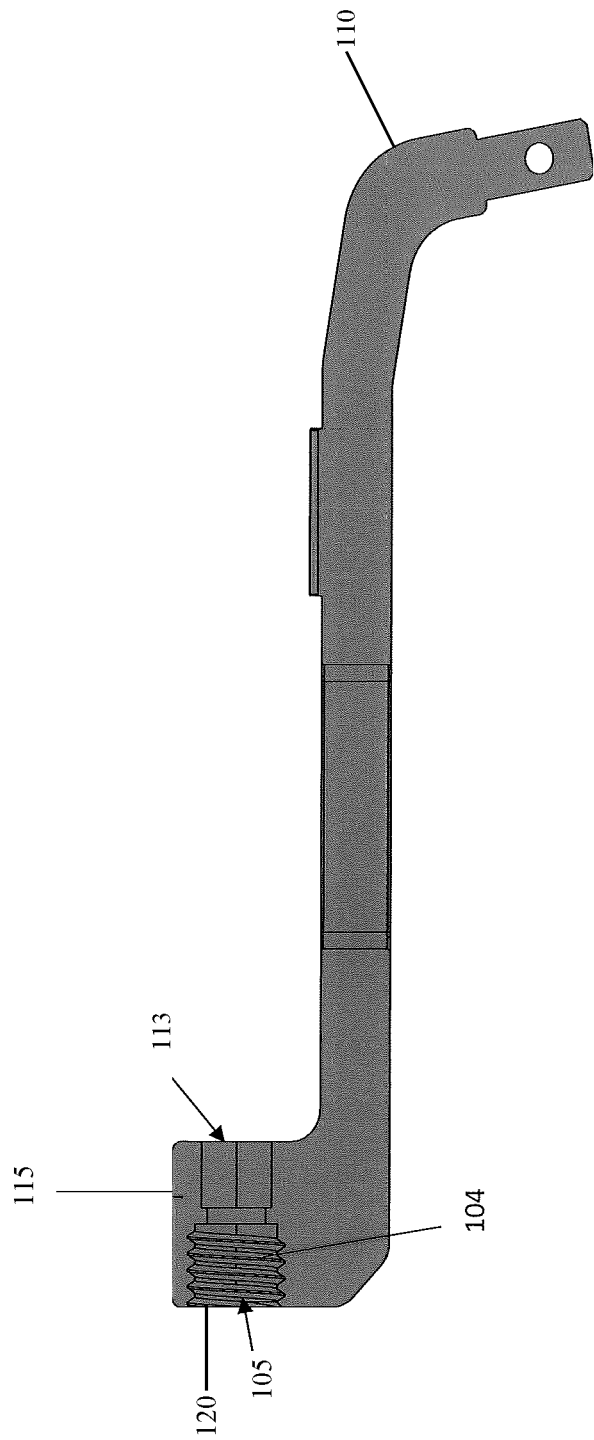
FIG. 4D illustrates a cross sectional view of the frame as described in one embodiment of the drill guide of the present disclosure.
Figure 5:
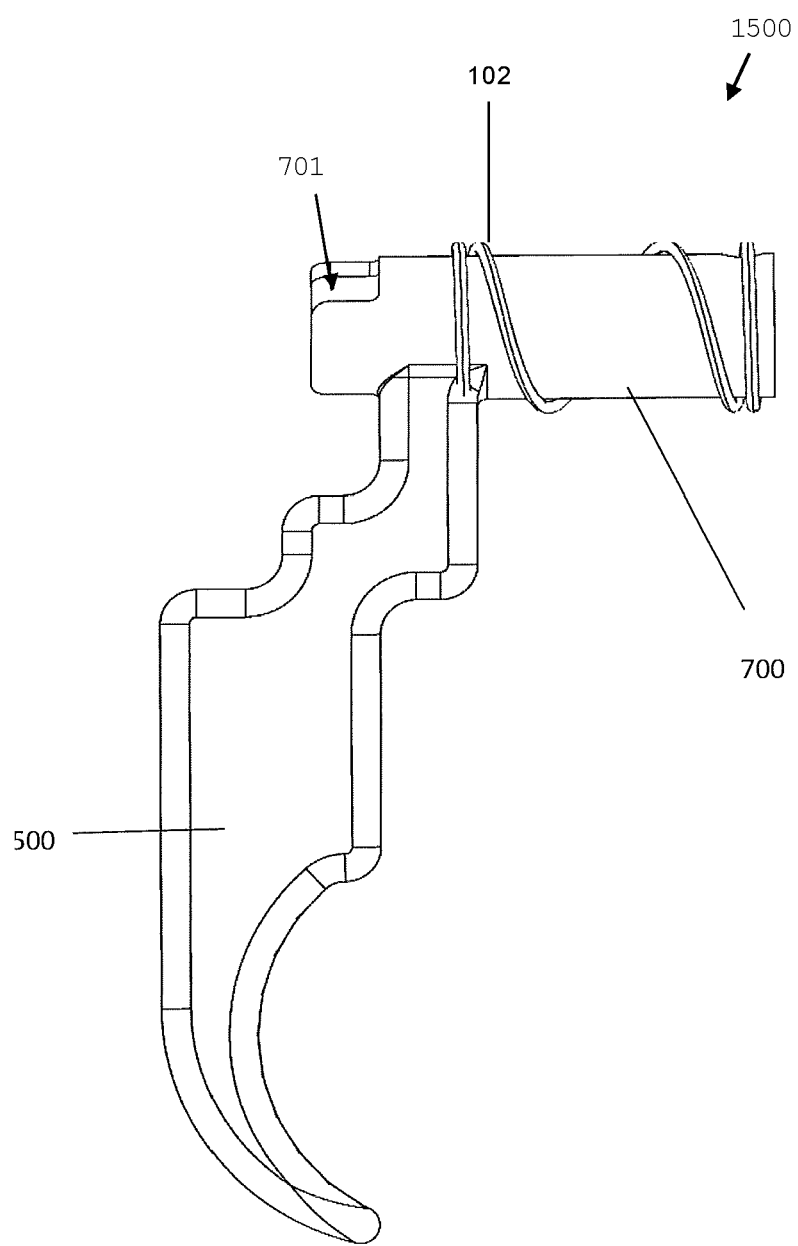
FIG. 5 shows a side view of the trigger assembly of one embodiment of the drill guide.
Figure 6A:
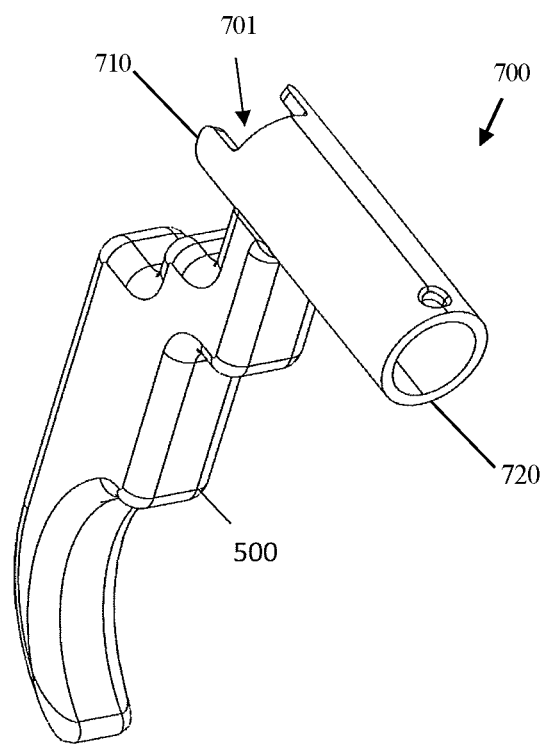
FIG. 6A illustrates an isometric view of the trigger and primary actuating element as described in one embodiment of the drill guide of the present disclosure.
Figure 6B:
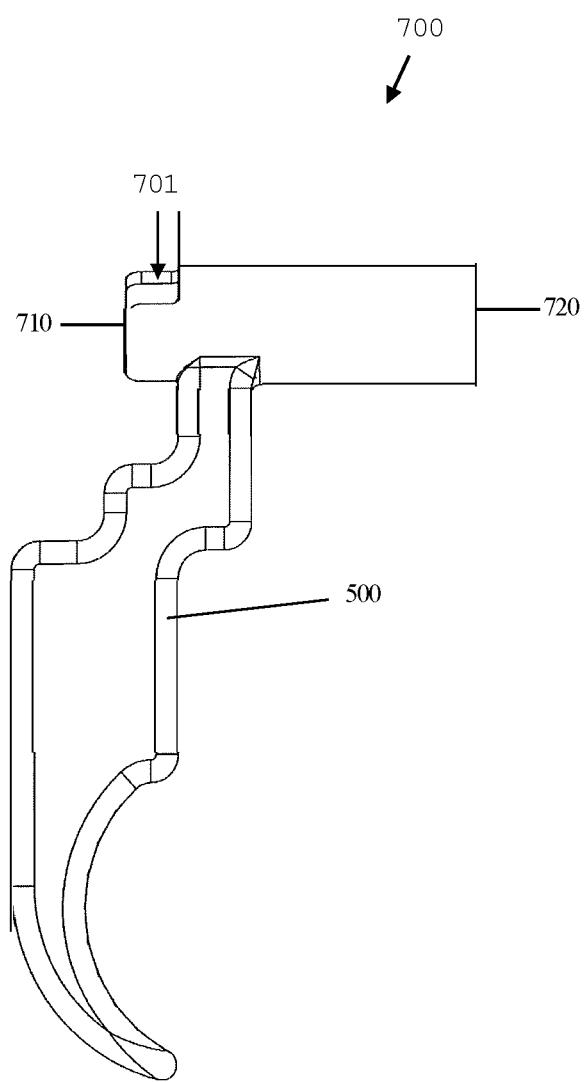
FIG. 6B illustrates a side view of the trigger and primary actuating element as described in one embodiment of the drill guide of the present disclosure.
Figure 7A:
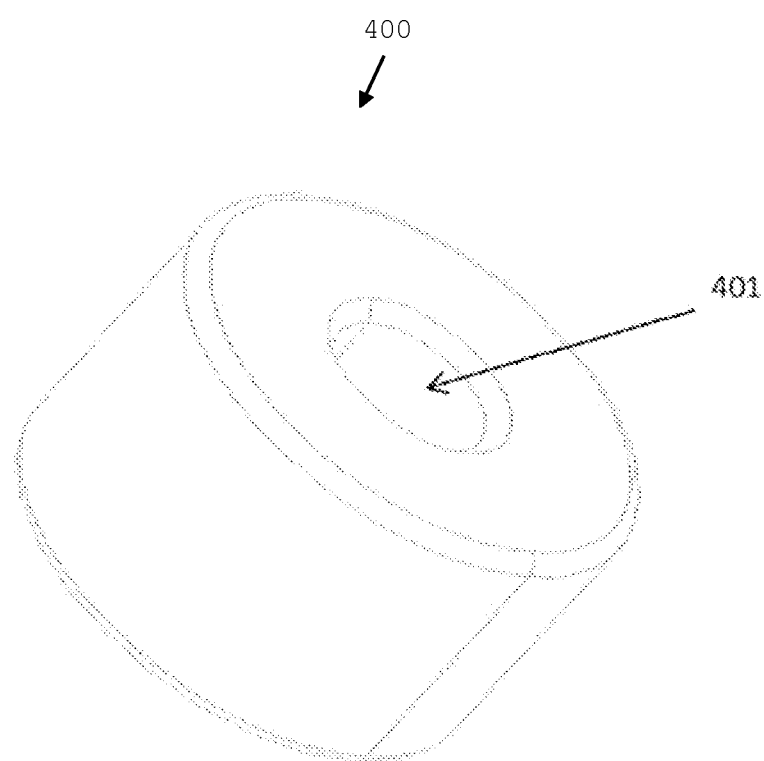
FIG. 7A illustrates an isometric view of the drill stop as described in one embodiment of the drill guide of the present disclosure.
Figure 7B:
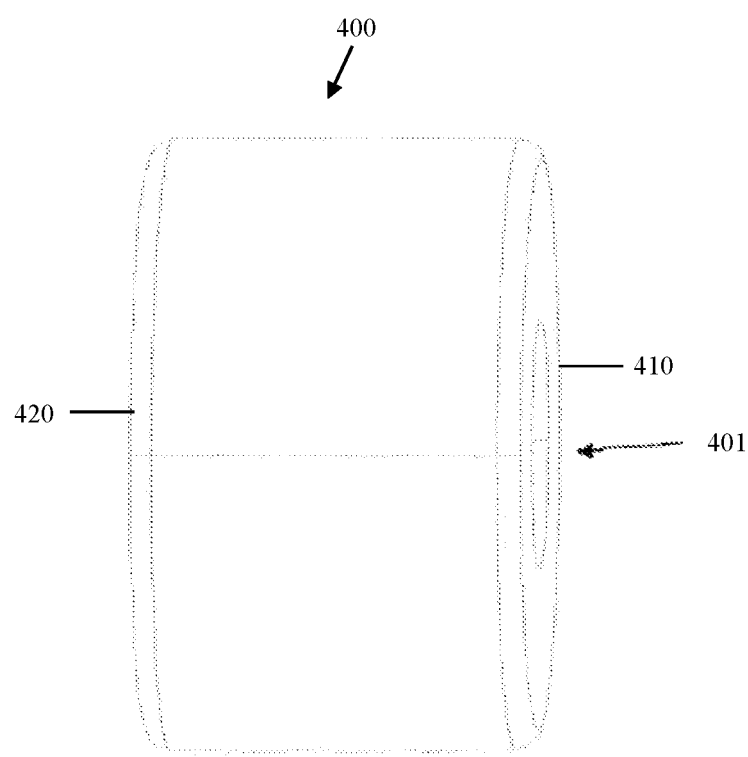
FIG. 7B illustrates a side view of the drill stop guide as described in one embodiment of the drill guide of the present disclosure.
Figure 9:
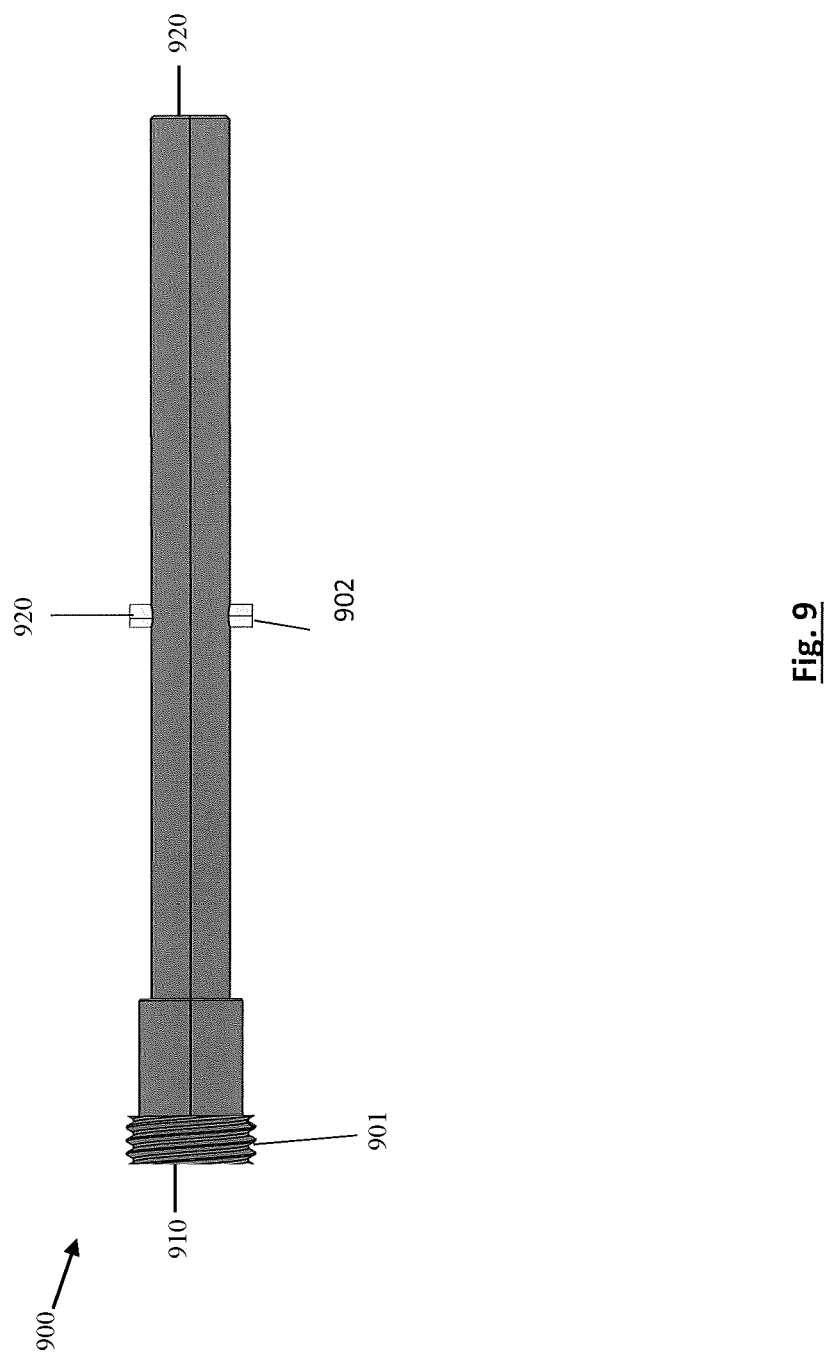
FIG. 9 illustrates a side view of the inner guide as described in one embodiment of the drill guide of the present disclosure.
Figure 10A:
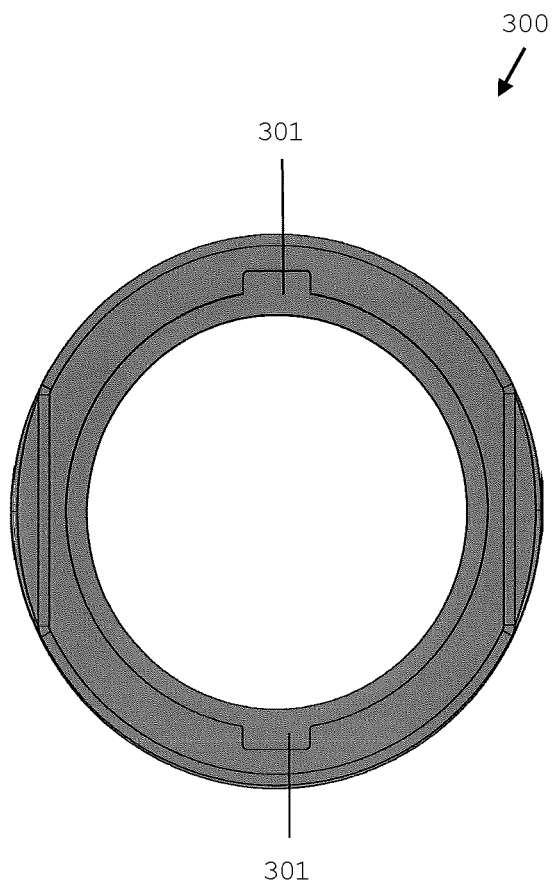
FIG. 10A illustrates a front view of the sheath as described in one embodiment of the drill guide of the present disclosure.
Figure 10B:
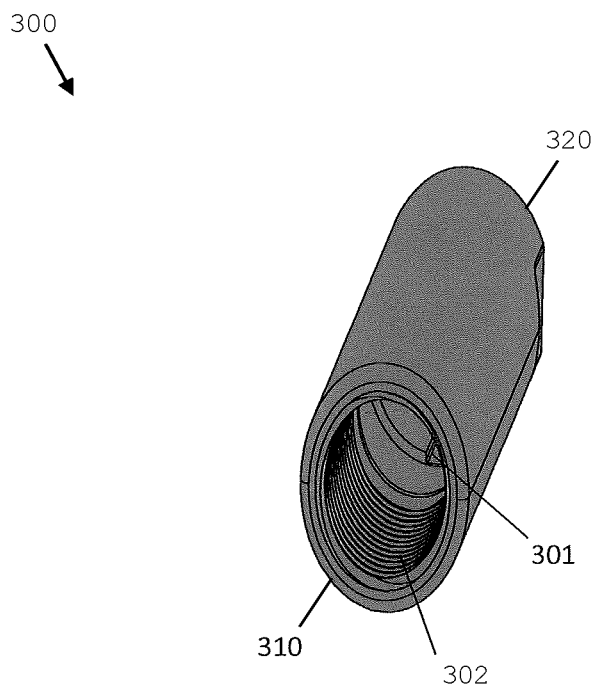
FIG. 10B illustrates an isometric view of the sheath from the proximal end as described in one embodiment of the drill guide of the present disclosure.
Figure 10C:
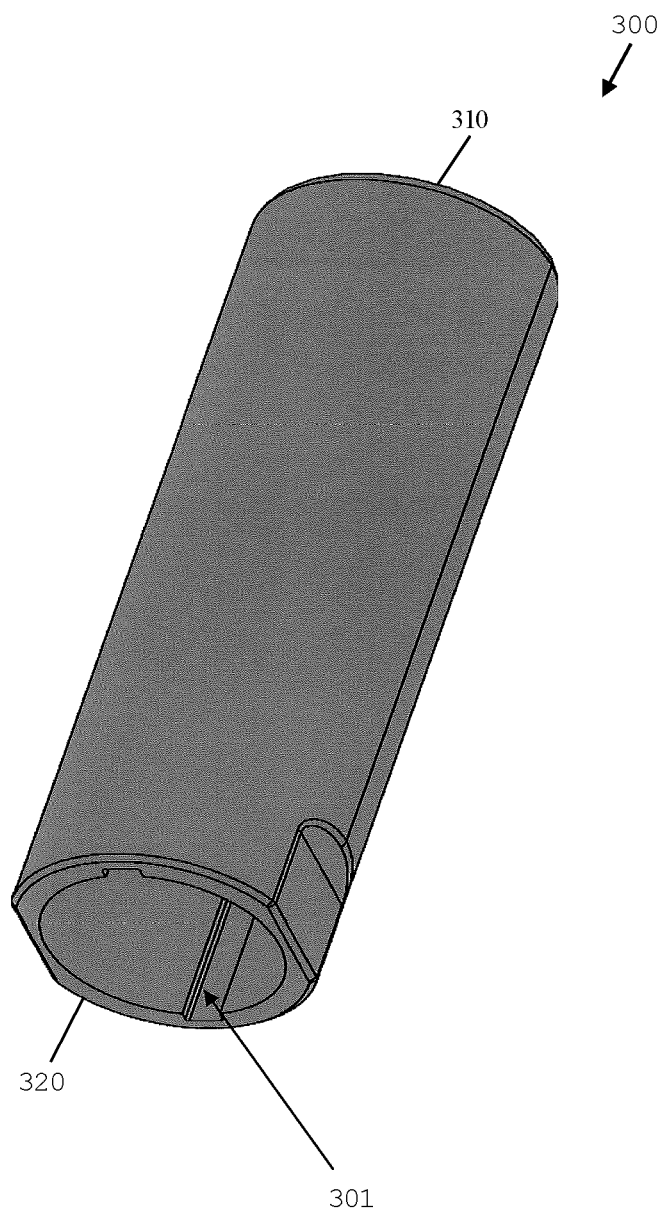
FIG. 10C illustrates an isometric view of the sheath from the distal end as described in one embodiment of the drill guide of the present disclosure.
Figure 11A:
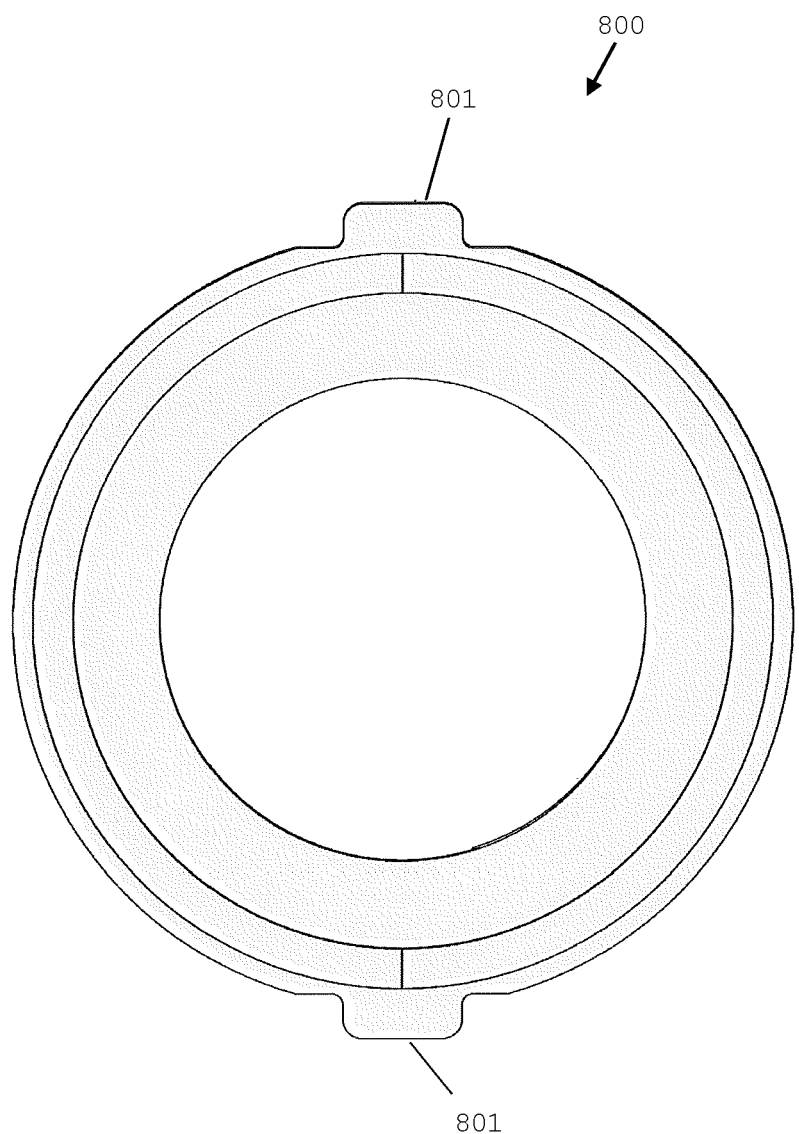
FIG. 11A illustrates a view of the intermediate actuating element from the proximal end as described in one embodiment of the drill guide of the present disclosure.
Figure 11B:
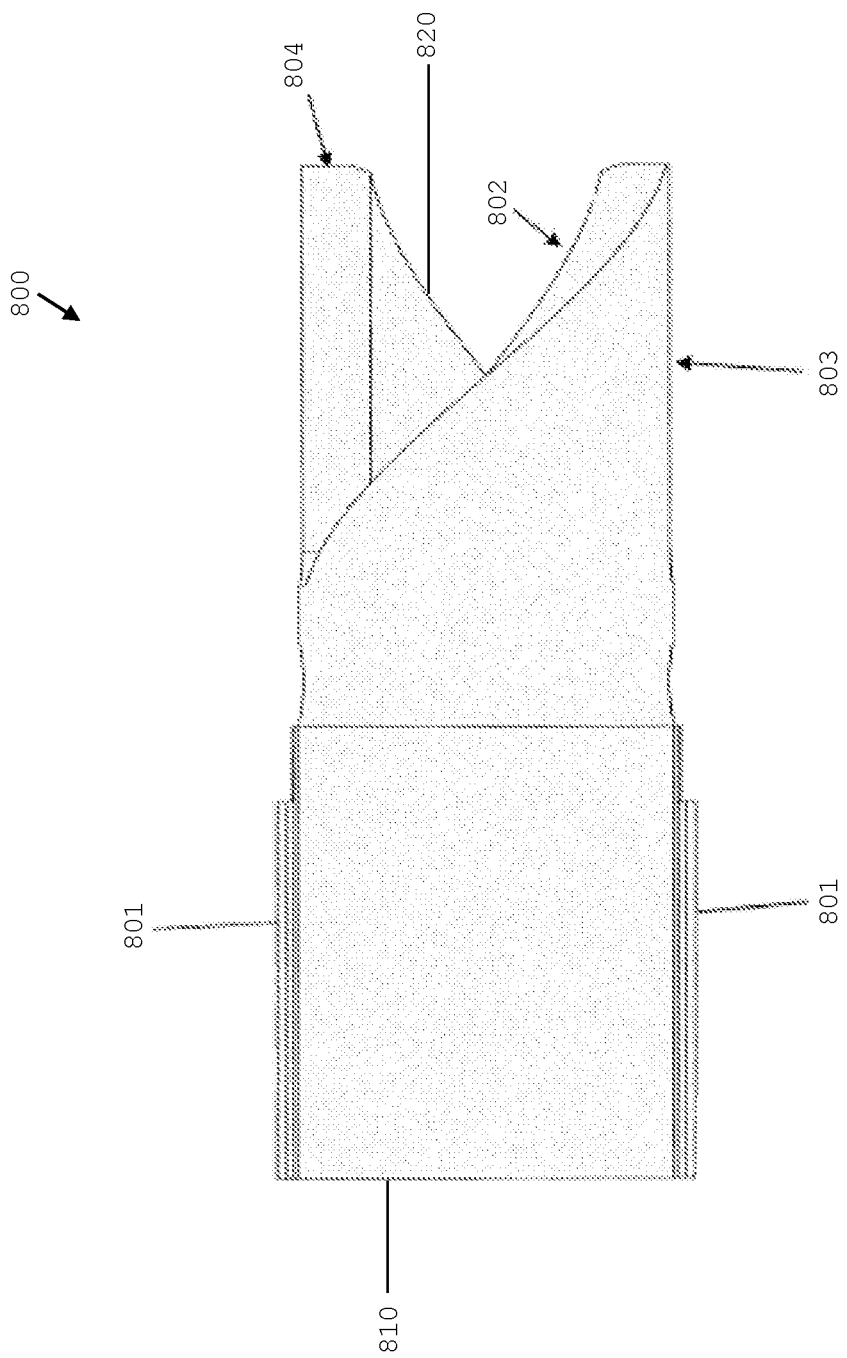
FIG. 11B illustrates a side view of the intermediate actuating element as described in one embodiment of the drill guide of the present disclosure.
Figure 11C:
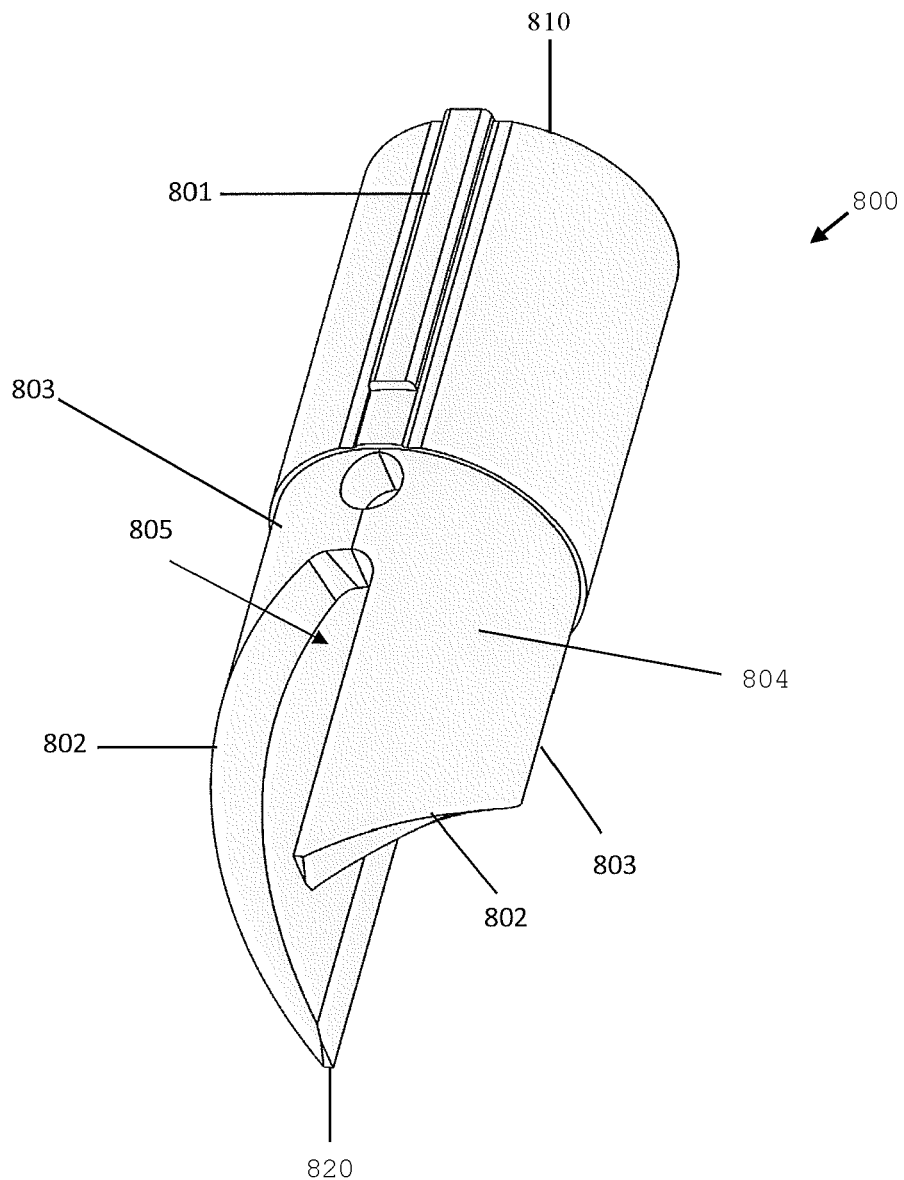
FIG. 11C illustrates an isometric view of the intermediate actuating element as described in one embodiment of the drill guide of the present disclosure.

The horizontal portion 116 of the frame 100 has an opening 103 that extends through the horizontal portion 116 and receives trigger 500. Additionally, the opening 103 must have a length sufficient to accommodate the lateral translation of the trigger 500 so that one trigger cycle (as discussed below) can be completed. Furthermore, located on the distal end 120 of the horizontal portion 116 of the frame 100 is the vertical element 115 of the frame 100. As shown in FIGS. 4A and 4B, the vertical element 115 includes a height 111, a width 107 and a thickness 108. As shown in FIGS. 4C and 4D, the vertical element 115 has a height 111 that is sufficient to include a distal opening 105. The distal opening 105 extends partially through the thickness 108 of the vertical element 115. The distal opening 105 has a diameter that will vary in size, but may coincide with the diameter a modular sheath 300 in alternative embodiments (as discussed below). Furthermore, the distal opening 105 may be fitted with a female thread 104 that allows the connection of the modular sheath 300 (as discussed below). Additionally, located on the opposite end of the vertical element 115 is the proximal opening 113. The proximal opening 113 has a diameter that will vary in size, but must coincide with the diameter of the inner guide 900.

In this embodiment, the shell 1200 also includes a shaft 200. As illustrated in FIG. 3, the shaft 200 is a hollow cylinder that is located adjacent to the vertical element 115 of the frame 100. The shaft 200 surrounds a number of internal elements (as discussed below). Additionally, the shaft 200 has a diameter that is sufficient to receive the sheath 300 upon lateral translation of the sheath 300 toward the distal end 1120 of the drill guide 1000.

The shell 1200 of this drill guide 1000 includes a drill stop 400. The drill stop 400 serves two primary purposes: 1) it provides a barrier for the drill to prevent plunging during use; and 2) allows the surgeon to reverse the depth by rotating the drill stop 400, and in turn the sheath 300, counter-clockwise. As illustrated in FIGS. 1, 2A, 2B, 3, 7A and 7B, the drill stop 400 is located on immediately adjacent to the proximal end 310 of the sheath 300. The drill stop 400 may encompass a portion of the sheath 300 in its static state as shown in FIGS. 1 and 3. The drill stop 400 also includes an opening 401 which allows the surgeon to insert the drill through the drill stop 400.

Figure 2A:
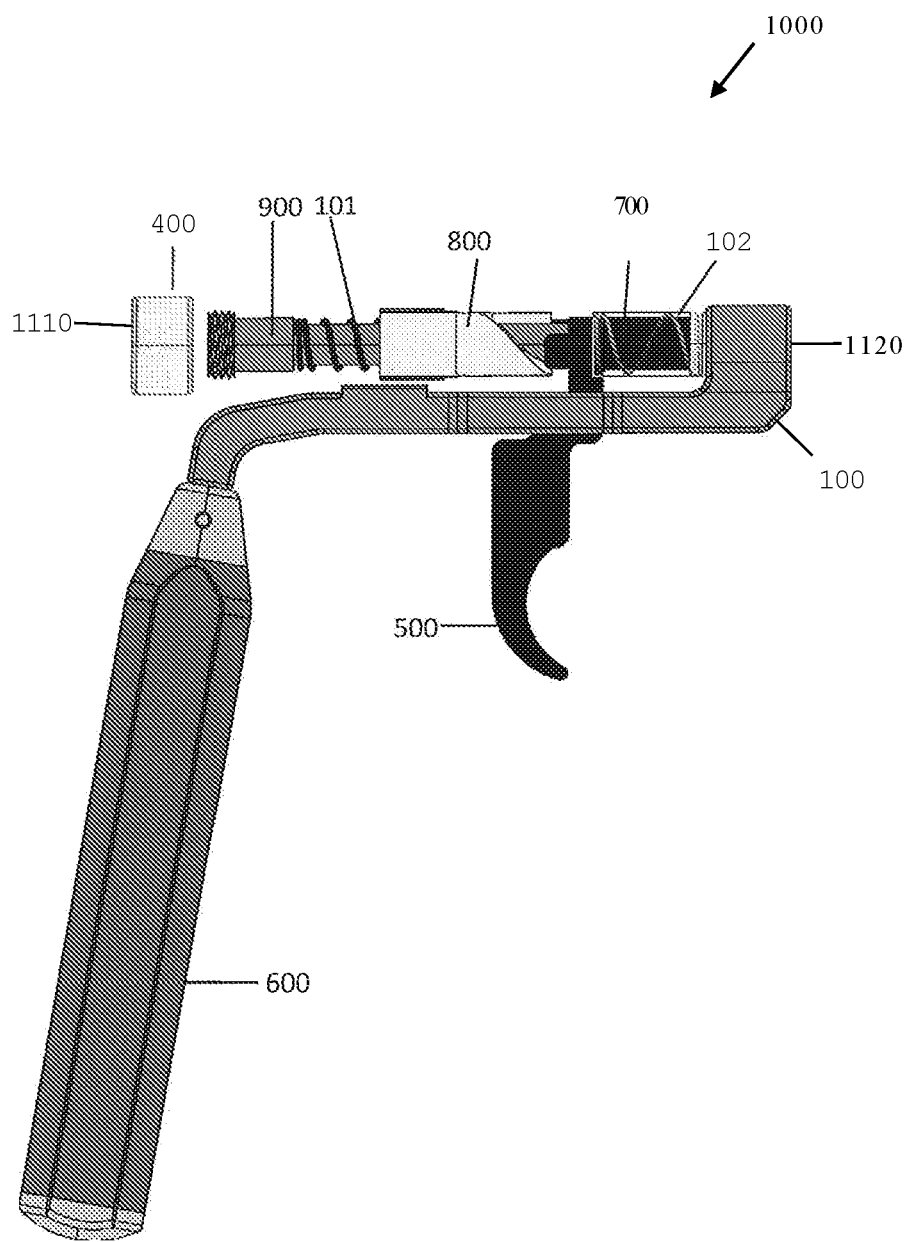
FIG. 2A illustrates a side view of one embodiment of the drill guide without the shaft and sheath so as to view the inner guide, the distal and proximal springs, the primary actuating element and the intermediate actuating element.
Figure 2B:
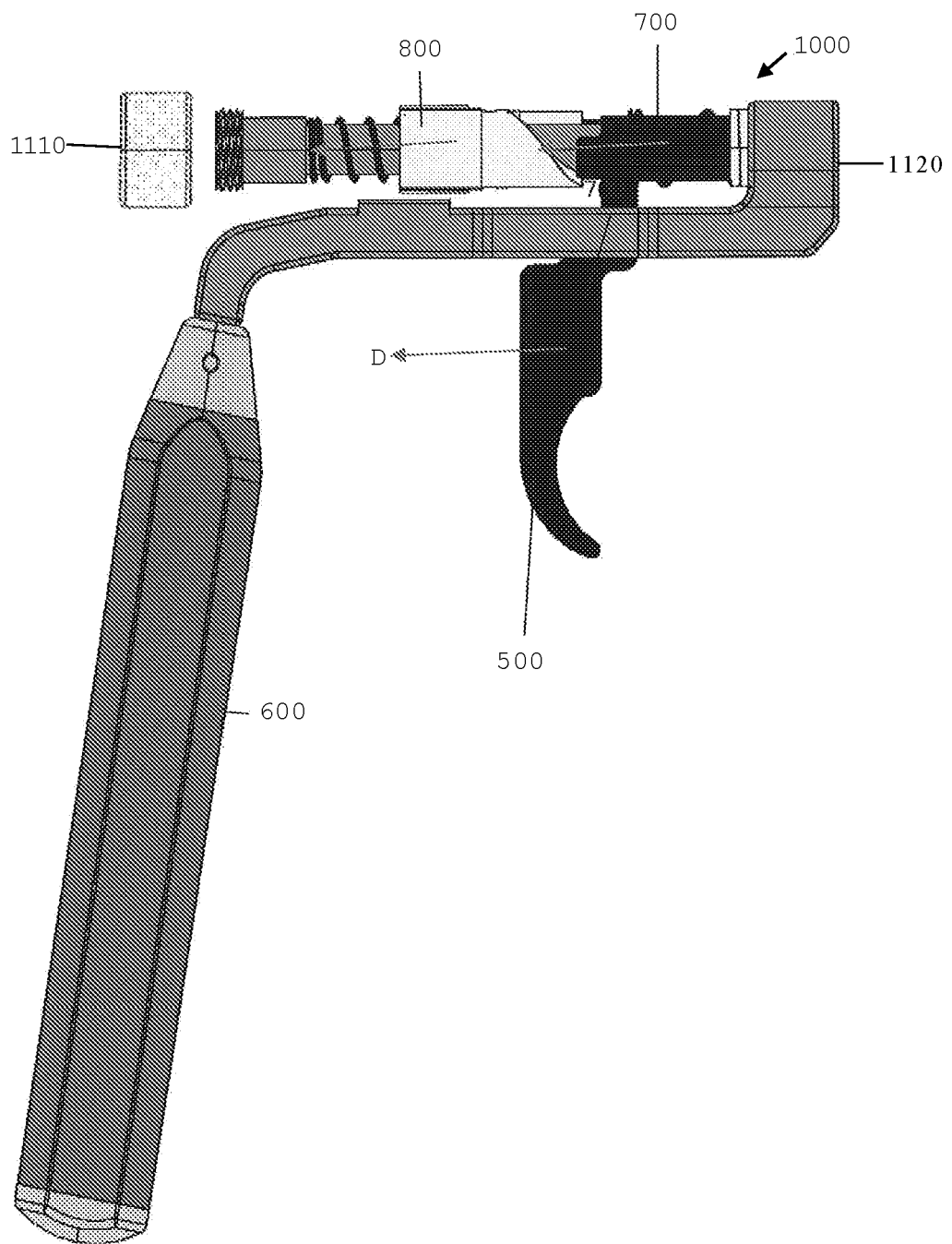
FIG. 2B illustrates the same elements of FIG. 2A; however, with the addition of illustrative arrows to show direction D of movement once a trigger cycle is initiated.

Enclosed in the shell 1200 of the drill guide 1000 is first, the trigger assembly 1500, comprised of a primary actuating element 700, a trigger 500, and a distal spring 102. According to the exemplary embodiment shown in FIGS. 5-6B, the trigger 500 and primary actuating element 700 are of unitary construction. As illustrated in FIGS. 1-2A, 5, 6A, and 6B, the trigger 500 is located immediately below the primary actuating element 700 and may perpendicular to the primary actuating element 700. The primary purpose of the trigger 500 is translate the primary actuating element 700 laterally toward the proximal end 1110 of the drill guide 1000 as shown in FIG. 2B. This is accomplished when the surgeon squeezes or pulls the trigger 500 toward the handle 600.

The primary actuating element 700 is a hollow cylinder. Located on the proximal end 710 of the primary actuating element 700 is a recess 701 designed to receive the control pin 902 once the primary actuating element 700 translates laterally toward the proximal end 1110 of the drill guide 1000. This recess 701 is large enough to accept the control pin 902 during translation of the primary actuating element 700 upon the initiation of the first trigger cycle.

Additionally, as illustrated in FIG. 3, the trigger assembly 1500 includes a distal spring 102 located toward the distal end 1120 of the drill guide 1000 and is located on the exterior of the primary actuating element 700. The distal spring 102 is attached to both the frame 100, and the primary actuating element 700. The distal spring 102 is designed to shore up any slack that may exist, but also assists in returning the primary actuating element 700 and trigger 500 in its resting location.

Finally, the drill guide 1000 also includes a telescopic rotational assembly 1600, illustrated in FIG. 8, comprised of an inner guide 900, a sheath 300, an intermediate actuating element 800, and a proximal spring 101. The telescopic rotational assembly 1600 is responsible for initiating the final step, ultimately responsible for depth adjustment.

The inner guide 900 serves the purpose of guiding the drill bit throughout the drill guide 1000. As illustrated in FIGS. 2A, 2B, 8, and 9, the inner guide 900 is a narrow cylinder with an opening 903 that extends throughout the length of the inner guide 900. The inner guide 900, itself, runs nearly the length of the shell 1200 of the drill guide 1000, beginning at the proximal end 310 of the sheath 300 and continuing throughout the drill guide 1000 into the vertical element 115 of the frame 100. Located on the proximal end 910 of the inner guide 900 is male threaded portion 901 which is threaded to the female threaded portion 302 of the sheath 300. Furthermore, located approximately midway on the inner guide 900 is a pair of control pins 902. The control pins 902 are placed in the slots 805 between the two arms 804 of the intermediate actuating element 800 and prevents rotation once the drill guide 1000 begins a trigger cycle.

In this embodiment, the telescopic rotational assembly 1600 also includes a sheath 300. The sheath 300, like the shaft 200, is also a hollow cylinder. As illustrated in FIGS. 8, 10A-C, located on the inner circumference of the sheath 300 at the distal end 320 of the sheath 300 is a pair of female rail slots 301 directly across from each other. The female rail slots 301 are a distance long enough to receive the male rails 801 of the intermediate actuating element 800 upon translation toward the proximal end 1110 of the drill guide 1000. Furthermore, located on the proximal end 310 of the sheath 300 is a female threaded portion 302. This threaded portion 302 interacts with the male threaded portion 901 of the inner guide 900 and allows the sheath 300 as a whole, to rotate and move within the shaft 200 to regulate and adjust the depth of the drill.

In addition to the aforementioned parts, the telescopic rotational assembly 1600 also contains an intermediate actuating element 800 which is adjacent to the primary actuating element 700. As illustrated in FIGS. 2A, 2B, 8, and 11A-C, the intermediate actuating element 800 is a hollow cylinder with two distinct arms 804 located on the distal end 820 of the intermediate actuating element 800. Located between the two arms 804 is a slot 805 large enough for the control pin 902 to rest prior to initiating a trigger cycle. Each arm 804 is configured so that each arm 804 has a spiraled, ramped portion 802 and a straightened portion 803. The two arms 804 are aligned so that the ramped, spiraled portion 802 of one arm 804, is adjacent to the straightened portion 803 of the arms 804, so that a slot 805 is formed between the spiraled portion 802 and the straightened portion 803 of the arms 804 and the control pin 902 may rest therein prior to the initiation of one trigger cycle.

Furthermore, located on the proximal end 810 of the intermediate actuating element 800 is a pair of male rails 801. These rails 801 are slidingly engaged with the female rail slots 301 located on the sheath 300. Upon lateral translation of the intermediate actuating element 800 toward the proximal end 1110 of the drill guide 1000, the rails 801 slide within the female rail slots 301 of the sheath 300.

Finally, the telescopic rotational assembly contains a proximal spring 101. The proximal spring 101 is located near the proximal end 1110 of the drill guide 1000 and wraps around the exterior of a portion of the inner guide 900. The proximal spring 101 is attached to both the inner guide 900 and the interior of the intermediate actuating element 800. Like the distal spring 102, the proximal spring 101 assists in returning the intermediate actuating element 800 to its resting position.

In regards to this embodiment, the drill guide 1000 is assembled as follows. The handle 600 is attached to the lower portion 116 of the proximal end 110 of the frame 100. The primary actuating element 700 is immediately adjacent to the vertical element 115 of the frame 100. Furthermore, the trigger 500, extends from the proximal end 710 of the primary actuating element 700 through the opening 103 of the frame 100. The trigger 500 is substantially parallel to the handle 600. The distal spring 102 wraps around the primary actuating element 700 and connects to both primary actuating element 700 and the vertical element 115 of the frame 100.

Immediately adjacent to the proximal end 710 of primary actuating element 700, is the intermediate actuating element 800. Prior to initiating a trigger cycle, the proximal end 710 of the primary actuating element 700 rests against the arms 804 of the intermediate actuating element 800 located on the distal end 820 of the intermediate actuating element 800. Furthermore, the intermediate actuating element 800 is partially covered by the adjacent sheath 300. The intermediate actuating element 800 fits within the sheath 300 via the male rails 801 which correspond with the female rail slots 301 of the sheath 300.

The intermediate actuating element 800, the primary actuating element 700, and the proximal spring 101 are all fully enclosed within the shaft 200. Located on the proximal end 310 of the sheath 300, is the drill stop 400. The drill stop 400 partially covers the proximal end 310 of the sheath 300. Beginning within the female threaded portion 302 of the sheath 300, is the male threaded portion 901 of the inner guide 900. The inner guide 900 then extends through the sheath 300, the opening of the intermediate actuating element 800 at the proximal end 810 and extending therethrough the distal end 820. Located on the inner guide 900 between the two arms 804 of the intermediate actuating element 800 are two control pins 902. The inner guide 900 continues through the opening of the primary actuating element 700, coming to a stop in the proximal opening 105 of the vertical element 115 of the frame 100.

With regards to the embodiment shown in FIG. 1, the drill guide 1000 is set to the initial depth prior to insertion into the surgical area. This is determined based on the surgeon's initial assessment and estimate of the appropriate bone screw length. The surgeon may then insert the drill through the drill stop 400 and the inner guide 900 wherein the drill will exit through the vertical element 115 of the frame 100. At this time, the surgeon may ascertain that the first pilot hole is not of a sufficient depth, and thus, requires a small, incremental adjustment. At this point, the surgeon may pull the trigger 500 of the drill guide 1000 once to complete one trigger cycle and thus, increase the depth of the drill.

Upon pulling the trigger 500 toward the handle 600, a series of events will occur before this trigger cycle is complete. First, the primary actuating element 700 will translate laterally toward the proximal end 1110 of the drill guide 1000. This action expands the distal spring 102. As the primary actuating element 700 translates toward the proximal end 1110 of the drill guide 1000, it simultaneously begins to translate the intermediate actuating element 800. In its static state, the straightened portion 803 of the arm 804 of the intermediate actuating element 800 rests against the control pins 902 located on the inner guide 900. The control pins 902, in combination with the straightened portion 803 of the arm 804, prevent premature rotation of the intermediate actuating element 800. Concurrently, the intermediate actuating element 800, via the male rail 801 located on the intermediate actuating element 800, slides within the female rail slot 301 of the sheath 300 during this translation. Additionally, translation of the intermediate actuating element 800 compresses the proximal spring 101.

Next, the primary actuating element 700, along with the intermediate actuating element 800, continue to translate to the proximal end 1110 of the drill guide 1000 until the control pin 902 no longer obstructs the rotation of the intermediate actuating element 800. Once the intermediate actuating element 800 translates past the control pins 902, and the control pins 902 clear the arm 804 of the intermediate actuating element 800, the control pins 902 will move into the recess 701 of the primary actuating element. At this point, the intermediate actuating element 800 is now partially covered by the sheath 300. Subsequently, the intermediate actuating element 800 will rotate 180.degree. clockwise. Simultaneously, the sheath 300 will also rotate clockwise.

Upon rotation of the intermediate actuating element 800, and in turn the sheath 300, the female threaded portion 302 of the sheath 300, interacts with the male threading 901 of the inner guide 900. The threading 302 of the sheath 300 will rotate along the threading 901 of the inner guide 900. This rotation will cause the sheath 300 to translate forward an incremental distance based on the pitch of the threading, telescopically into the shaft 200. As the drill stop 400 is attached to the sheath 300, the drill stop 400 also translates toward the distal end of the drill guide 1000, allowing the surgeon to drill deeper. For purposes of this embodiment, the incremental distance is 1 mm. The surgeon will hear a "click" to signal that the trigger cycle is complete.

Upon completion of one trigger cycle and release of the trigger 500, the compressed proximal spring 101, exerts force in the direction of the distal end 1120 of the drill guide 1000. Simultaneously, the distal spring 102 returns to its static state. These simultaneous actions, in combination with the control pins 902, prevent multiple, unintended rotations of the intermediate actuating element 800. As a result, the intermediate actuating element 800 and the primary actuating element 700 return to their original locations. The surgeon is free to repeat the aforementioned actions as needed to reach the appropriate depth.

The drill guide 1000 also allows the surgeon to reverse the adjustment. This is accomplished when the surgeon rotates the drill guide stop 400 in the counter-clockwise direction. The counter-clockwise rotation of the drill stop guide 400 rotates the sheath 300, and in turn, the intermediate actuating element 800 counter-clockwise. During this counter-clockwise rotation, the control pins 902, slide up the spiral ramps 802 of the intermediate actuating element 800. The rotation of the sheath 300 interacts with the inner guide 900 and translates the sheath 300 proximally. As a result, the drilling depth is decreased an incremental amount. Similar to the clockwise rotation, the surgeon will hear a click once the control pins 902 reach the end of the spiral and pop into the adjacent slot 805 to signal that one reverse trigger cycle is complete.

Figure 12:
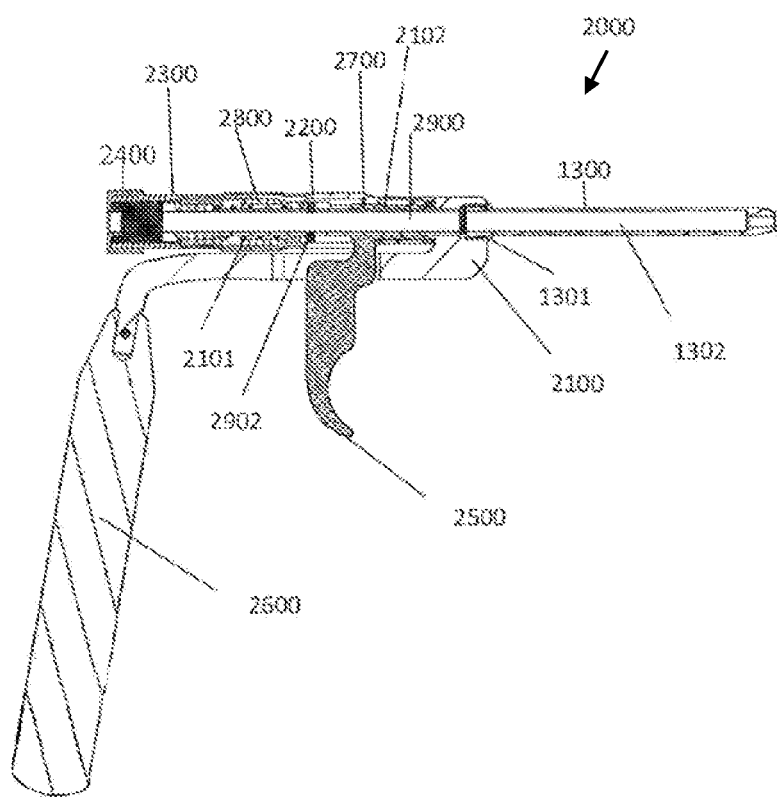
FIG. 12 illustrates a cross sectional side view of an alternative embodiment of the drill guide of the present disclosure.

Additional embodiments of the present disclosure describe an adjustable depth drill guide 2000 that is configured for allowing surgeons to make incremental depth adjustments in small increments when drilling pilot holes prior to bone screw placement. The adjustable depth drill guide 2000 as illustrated in FIG. 12 comprises: a handle 2600; an inner guide 2900; a modular sleeve 1300; a sheath 2300; an intermediate actuating element 2800; a primary actuating element 2700; a trigger 2500; a drill stop 2400; a frame 2100; an shaft 2200; a plurality of control pins 2902; and a proximal spring 2101; and a distal spring 2102.

The configuration of this embodiment is identical to that of the original sans the addition of the modular sleeve 1300. The modular sleeve 1300 contains a threaded portion 1301. This threaded portion 1301 may be affixed to the frame 100 via the distal opening 105 of the vertical element 115 of the frame 100. The distal opening 105 is threaded 104 so that the modular sleeve 1300 may be affixed to the drill guide 1000. The addition of the modular sleeve 1300 allows the surgeon to drill at various angles. Further, the modular sleeve 1300 can be configured to mate with various implants or anatomy. The modular sleeve 1300, similar to the inner guide 900 is a hollow cylinder with an opening 1302 that extends throughout the length of the modular sleeve 1300.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow.

Similarly, this method of disclosure, is not to be interpreted as reflecting an intention that any claim require more features than are expressly recited in that claim. Rather, as the following claims reflect, inventive aspects lie in a combination of fewer than all features of any single foregoing disclosed embodiment. Thus, the claims following the Detailed Description are hereby expressly incorporated into this Detailed Description, with each claim standing on its own as a separate embodiment.

What is claimed is:

1. A method for drilling a hole within a surgical area, the method comprising:
    providing a drill guide including:
        a trigger,
        a primary actuating element, and
        an intermediate actuating element adjacent to the primary actuating element;
    actuating the trigger of the drill guide to cause rotation of the intermediate actuating element; and
    adjusting a drill depth of the drill guide.

2. The method of claim 1, wherein actuating the trigger of the drill guide causes translation of the primary actuating element and the intermediate actuating element in a proximal direction.

3. The method of claim 1, further comprising coupling a sheath of the drill guide to the intermediate actuating element via one or more rails.

4. The method of claim 3, wherein the rotation of the intermediate actuating element causes distal advancement of the sheath of the drill guide.

5. The method of claim 3, further comprising threadedly coupling the sheath of the drill guide to an inner guide of the drill guide.

6. The method of claim 5, wherein the rotation of the intermediate actuating element is about the inner guide.

7. The method of claim 1, wherein the primary actuating element comprises a hollow cylinder and the intermediate actuating element comprises a hollow cylinder with one or more arms at its distal portion.

8. The method of claim 1, wherein actuating the trigger of the drill guide comprises actuating the trigger of the drill guide using only one hand of a user.

9. The method of claim 1, wherein actuating the trigger of the drill guide comprises actuating the trigger of the drill guide when the drill guide is within the surgical area.

10. The method of claim 1, further comprising:
    providing an audio signal to indicate completion of a trigger cycle for adjusting the drill depth.

11. A method for drilling a hole within a surgical opening, the method comprising:
    placing a drill guide over the surgical opening, the drill guide comprising:
        a trigger,
        a primary actuating element connected to the trigger, and
        an intermediate actuating element adjacent to the primary actuating element,
    actuating the trigger of the drill guide to cause rotation of the intermediate actuating element,
    wherein the drill guide is configured to allow drilling depth adjustment without removing the drill guide from the surgical opening.

12. The method of claim 11, wherein actuating the trigger of the drill guide comprises actuating the trigger of the drill guide using only one hand of a user.

13. The method of claim 11, wherein actuating the trigger of the drill guide comprises completing a trigger cycle and adjusting the drilling depth by a predetermined distance.

14. The method of claim 11, wherein actuating the trigger causes translation of the primary actuating element and the intermediate actuating element in a proximal direction.

15. The method of claim 11, further comprising coupling a sheath of the drill guide to the intermediate actuating element via one or more rails.

16. The method of claim 15, wherein the rotation of the intermediate actuating element causes distal advancement of the sheath of the drill guide.

17. The method of claim 15, further comprising threadedly coupling the sheath of the drill guide to an inner guide of the drill guide.

18. The method of claim 17, wherein the rotation of the intermediate actuating element is about the inner guide.

19. The method of claim 11, wherein the rotation of the intermediate actuating element is about 180 degrees.

20. The method of claim 11, further comprising:
    providing an audio signal to indicate completion of a trigger cycle for adjusting the drill depth.

* * * * *